United States Patent [19]

DeLuca et al.

[11] 4,260,549
[45] Apr. 7, 1981

[54] PROCESS FOR PREPARING 1α-HYDROXYLATED COMPOUNDS

[75] Inventors: Hector F. DeLuca; Heinrich K. Schnoes, both of Madison; Herbert E. Paaren, Verona; David E. Hamer, Madison, all of Wis.

[73] Assignee: Wisconsin Alumni Research Foundation, Madison, Wis.

[21] Appl. No.: 41,079

[22] Filed: May 21, 1979

[51] Int. Cl.³ .............................................. C07J 9/00
[52] U.S. Cl. ................................ 260/397.2; 260/397.1
[58] Field of Search ...................................... 260/397.2

[56] References Cited

U.S. PATENT DOCUMENTS

| 3,743,661 | 7/1973 | De Luca et al. | 260/397.2 |
| 3,887,545 | 6/1975 | Iacobelli et al. | 260/397.2 |
| 4,038,272 | 7/1977 | Partridge, Jr. et al. | 260/397.2 |
| 4,179,452 | 12/1979 | Ochi et al. | 260/397.2 |

FOREIGN PATENT DOCUMENTS 1463985  2/1977  United Kingdom ................. 260/397.2

OTHER PUBLICATIONS

Paaren et al., Proc. Natl. Acad. Sc. USA, vol. 75, No. 5, pp. 2080-2081 (May 1978).
Napoli et al., "Steroids" vol. 32, No. 4 (Nov. 1978) pp. 453-465.
PCT-International Publication No. WO/79/00513, Aug. 9, 1979.
"Steroids" Aug. 1977, article by Pele, pp. 193-200.

Primary Examiner—Elbert L. Roberts
Attorney, Agent, or Firm—Howard W. Bremer

[57] ABSTRACT

An improved method for the preparation of 1α-hydroxylated vitamin D compounds involving directly introducing an oxygen function at carbon 1 of the vitamin D molecule or precursors or derivatives thereof, wherein the 1α-hydroxycyclovitamin D intermediate is solvolyzed directly, without first converting the 1-hydroxy group to a 1-O-acyl function as a protective measure.

12 Claims, No Drawings

PROCESS FOR PREPARING 1α-HYDROXYLATED COMPOUNDS

The invention described herein was made in the course of work under a grant or award from the Department of Health, Education, and Welfare.

DESCRIPTION

1. Technical Field

This invention relates to a method for preparing compounds having vitamin D-like activity and to compounds which are key intermediates in such method.

More specifically, this invention relates to a method for preparing compounds having vitamin D-like activity which contain an oxygen function at carbon 1 in the molecule.

Still more specifically, this invention relates to a method for preparing 1α-hydroxylated compounds which are characterized by vitamin D-like activity via a cyclovitamin D intermediate.

It is well known that the D vitamins exhibit certain biological effects, such as stimulation of intestinal calcium absorption, stimulation of bone mineral resorption and the prevention of rickets. It is also well known that such biological activity is dependent upon these vitamins being altered in vivo, i.e. metabolized, to hydroxylated derivatives. For example, current evidence indicates that 1α,25-dihydroxyvitamin $D_3$ is the in vivo active form of vitamin $D_3$ and is the compound responsible for the aforementioned biological effects.

The synthetic 1α-hydroxyvitamin D analogs, such as 1α-hydroxyvitamin $D_3$, and 1α-hydroxyvitamin $D_2$ also exhibit pronounced biological potency and such compounds as well as the natural metabolites show great promise as agents for the treatment of a variety of calcium metabolism and bone disorders, such as osteodystrophy, osteomalacia and osteoporosis.

2. Background Art

The discovery that in vivo metabolism of vitamin D leads to 1α-hydroxylated forms and the demonstration that the presence of a 1α-hydroxy function imparts high biological potency to vitamin D compounds has lead to many processes for the chemical synthesis of such 1-hydroxylated derivatives. Most processes involve 1-hydroxylation of a suitable steroid precursor followed by conversion of 1-hydroxy steroid to the 1-hydroxyvitamin D compound. Recently a novel general scheme for the production of 1-hydroxylated vitamin D compounds has been proposed which differs radically from the methods previously known. This new process, developed by Paaren et al (Proc. Nat. Acad. Sci. U.S.A. 75, 2080–2081) involves the direct hydroxylation of a vitamin D precursor to give the corresponding 1α-hydroxy compound in high yield.

For purposes of discussion this process may be illustrated by the following schematic (Process Schematic A).

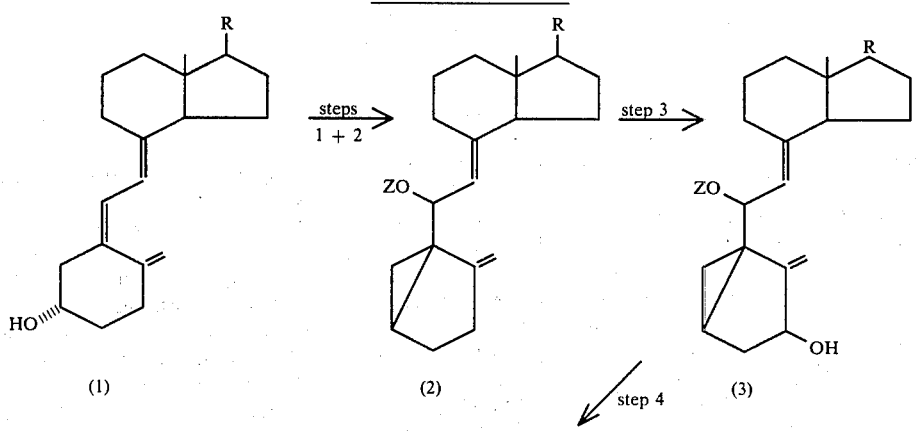

-continued
Process Schematic A

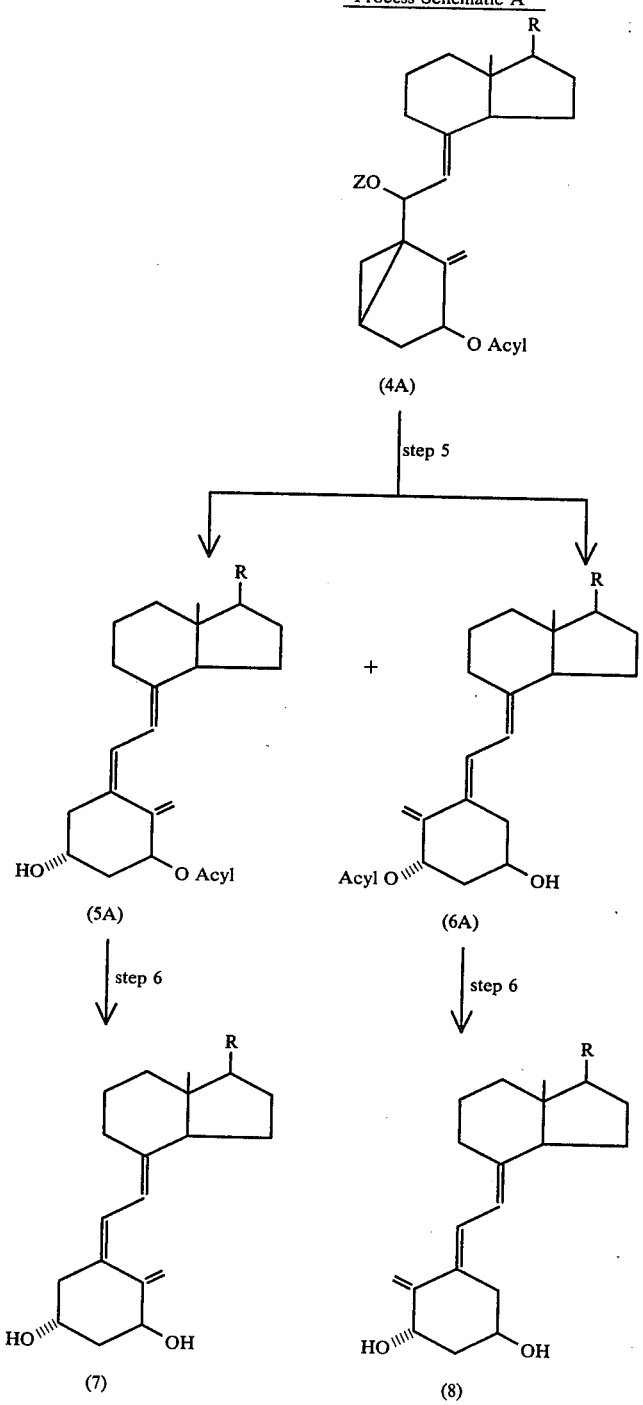

In reference to the foregoing schematic the process steps are:

Step (1): Tosylation of a β-hydroxyvitamin D starting material (e.g. vitamin D₃, vitamin D₂, 25-hydroxyvitamin D₃, etc.) to give the corresponding 3-O-tosyl derivative which is subjected directly to Step (2): Solvolysis in an alcohol solvent (ZOH, where Z may be methyl, ethyl, propyl, etc. or H) to give the cyclovitamin intermediate (2)

Step (3): Introduction of 1α-hydroxyl by allylic oxidation using SeO₂ to give intermediate (3)

Step (4): Protection of the 1α-hydroxy function as the 1α-O-acyl derivative (4A) where acyl may be any convenient acyl group such as formyl, acetyl, benzoyl, etc.

Step (5): Solvolysis of intermediate (4A) using p-toluene sulfonic acid, a catalyst, to form a mixture of 1α-O-acyl-3β-hydroxyvitamin D compound (5A) and the corresponding 5,6-trans isomer (6A)

Step (6): Separation of this mixture by chromatography and alkaline hydrolysis (or reductive cleavage) of the acyl function to produce the 1α-hydroxyvitamin D compound (7) and if desired, the corresponding 5,6-trans compound (8)

This process offers a highly convenient and efficient route to 1α-hydroxyvitamin D compounds (and/or their 5,6-trans isomers) from appropriate vitamin D starting materials. Furthermore, the method is extremely general in that the side chain R of the starting material may be any of the common side chains which may also be substituted by a wide spectrum of functional groups including hydroxy, alkyl, O-acyl, halo, keto, carboxy, amido, or unsaturation.

DISCLOSURE OF INVENTION

A new process has now been found which improves and shortens the Paaren et al process described above.

Specifically, it has been found that under suitable conditions the 1α-hydroxycyclovitamin D intermediate (structure 3 in the above schematic) can be solvolyzed directly—without prior protection of the 1-hydroxy group as 1-O-acyl function—to yield a mixture of 5,6-cis and 5,6-trans 1α-hydroxy-3-O-acyl vitamin D compounds, which can be separated and converted to the desired 1α-hydroxyvitamin D compounds (or the corresponding 5,6-trans isomer).

It is evident that Paaren et al protected the 1α-hydroxy function group by conversion to a 1α-O-acyl group, because of the reasonable expectation that the sensitive allylic 1α-hydroxy function would be subject to degradative reaction during solvolysis using a fairly strong acid such as p-toluene sulfonic acid. Experience has, in fact, shown that solvolysis of an unprotected 1α-hydroxycyclovitamin D compound under such conditions leads to much decomposition and a complex product mixture containing undesired products. Paaren et al indicate also that after protection of the 1α-hydroxyl as a 1α-O-acyl group the desired solvolysis product is obtained in good yield but such protection does not completely prevent undesired decomposition reaction during solvolysis using a p-toluene sulfonic acid catalyst. They further found that decomposition can be minimized by solvolyzing the 1α-O-acyl-protected cyclovitamin compound in acetic or formic acid. However, under such conditions they obtained the 5,6-cis and 5,6-trans mixture of the 1,3-di-O-acyl vitamin D compounds which is very difficult to separate, and the advantage of minimizing decomposition reactions is negated by the losses incurred due to the requirement for elaborate chromatography. Whenever the substituents at C-1 and C-3 are of like character (e.g. both are hydroxy or O-acyl) separation of the 5,6-cis and trans forms of such vitamin D derivatives is difficult. To overcome this separation problem, Paaren et al suggested a scheme in which a 1α-O-acyl cyclovitamin D compound (where acyl may represent any acyl group but not formyl) is solvolyzed in formic acid to produce the 5,6-cis and 5,6-trans mixture of the 1α-O-acyl-3β-O-formyl-vitamin D compounds. The formyl group is then removed by selective hydrolysis to yield the 5,6-cis and 5,6-trans mixture of the 1α-O-acyl-3β-hydroxy compounds, which may then be separated conveniently and processed according to step 6 of the above schematic. Such modification, however, introduces still another reaction step (the selective hydrolysis of the formyl group).

It is a particularly advantageous feature of the present process that it eliminates both the undesired decomposition reactions and the necessity for the hydroxy protection/deprotection steps. The process of this invention can be illustrated by the following schematic (Process Schematic B).

Process Schematic B

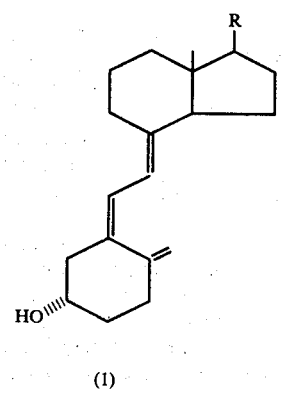
(1)

steps 1,2,3
as in Process
Schematic A

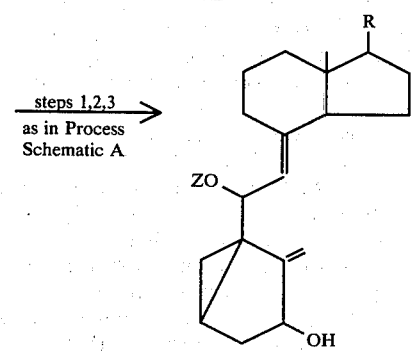
(3)

step 4

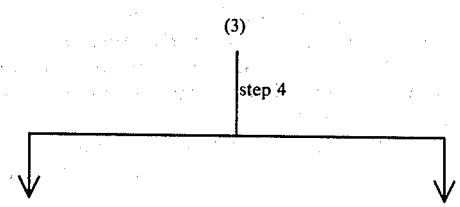

Process Schematic B

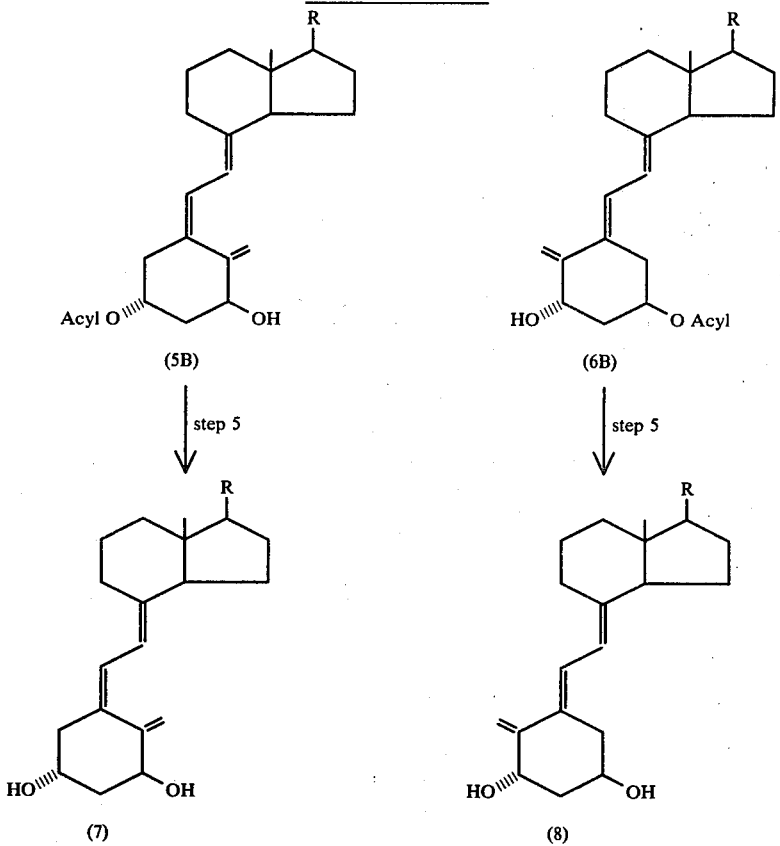

In the new process illustrated above, steps 1, 2 and 3 are identical to the corresponding steps in Process Schematic A.

Step 4 is the key new step which involves direct solvolysis of the 1α-hydroxycyclovitamin D intermediate (3) in the presence of low-molecular weight organic carboxylic acids (such as formic or acetic acids) to yield the 1α-hydroxy-3-O-acyl vitamin D derivative (5B) as well as the corresponding 1α-hydroxy-3-O-acyl-5,6-transvitamin D compound (6B) (where the acyl group corresponds, of course, to the acyl moiety of the acid used in the solvolysis reaction).

Step 5 is analogous to step 6 of Process Schematic A and involves the separation of the cis and trans 1α-hydroxy-3-O-acyl compounds and subsequent hydrolytic or reductive removal of the 3-acyl group to yield the 1α-hydroxyvitamin D compound (7) or, if desired, the 5,6-trans-1α-hydroxyvitamin D compound (8).

The process of this invention offers significant practical advantages over that of Paaren et al. Thus, (a) the overall synthesis is accomplished in fewer steps, since the hydroxy protection step and/or the formate hydrolysis step, or both, are omitted.

(b) direct solvolysis yields a product mixture containing the 1α-hydroxy-3-O-acyl vitamin D compound and the corresponding 5,6-trans product, without the contamination by various degradation products that results from the use of p-toluene sulfonic acid as a catalyst in the solvolysis reaction described by Paaren et al.

(c) because undesired degradation products are eliminated, separation of the cis and trans forms resulting from solvolysis is simplified.

(d) the brevity of the scheme and the ease of separation of cis and trans isomers makes the new scheme the preferred process for large-scale synthesis of 1α-hydroxyvitamin D compounds.

(e) the elimination of one process step and the absence of undesired degradation products leads to improved yields of desired 1α-hydroxylated compounds.

In the present process the steps up to the formation of the 1α-hydroxy cyclovitamin D intermediate (steps 1, 2, 3 in Process Schematic B) are, as already pointed out above, identical with the corresponding steps in the Paaren et al process (Process Schematic A) and are conducted as described by these authors.

The key new step, direct solvolysis of the 1α-hydroxy cyclovitamin D intermediate (step 4 of Process Schematic B) is conveniently accomplished by dissolving the cyclovitamin in a low-molecular weight organic carboxylic acid and briefly warming the resulting mixture. Preferred acids are, for example, formic or acetic acid and the reaction is conveniently conducted at a temperature of 40°–60° C. over a period of 15–30 minutes. If convenient, or required, an inert co-solvent may be used in conjunction with the organic carboxylic acid to improve the solubility of the 1-hydroxycyclovitamin. Suitable co-solvents are, for example, tetrahydrofuran or dioxane. Solvolysis of 1α-hydroxycyclovitamin D compounds in organic carboxylic acids results in a product mixture (ratio of ca. 3:1) consisting of 1α-hydroxy-3-O-acyl vitamin D and 1α-hydroxy-3-O-acyl-5,6-trans-vitamin D, where the acyl group derives from the organic acid used for solvolysis. For example, solvolysis of 1α-hydroxy-3,5-cyclovitamin $D_3$ in glacial acetic acid yields 1α-hydroxyvitamin $D_3$ 3-acetate and 1α-hydroxy-5,6-trans-vitamin $D_3$ 3-acetate. Similarly, solvolysis of 1α,25-dihydroxy-3,5-cyclovitamin $D_3$ in formic acid leads to 1α,25-dihydroxyvitamin $D_3$ 3-formate and the corresponding 5,6-trans isomer. The introduction of a 3-O-acyl function during solvolysis is a highly desirable and advantageous feature of the process, because the 5,6-cis and 5,6-trans isomers of 1α-hydroxy-3-O-acyl-vitamin D compounds are easily separated by chromatography. Suitable chromatographic methods include silica gel thin-layer chromatography, high pressure liquid chromatography and (for larger scale preparations) silica gel column chromatography or high pressure liquid chromatography using preparative columns, all of which are well known in the art.

After separation of the cis and trans isomers the 3-O-acyl group can be removed by hydrolysis under basic conditions, or by reduction using hydride reagents. For example treatment of a methanol solution of a 1α-hydroxy-3-O-acyl-vitamin D compound with 5% aqueous NaOH, for 1-2 hours at 25°-50° C., removes the acyl group quantitatively and yields the desired 1,3-dihydroxyvitamin D product. The same result is achieved by treatment of an ether solution of a 1α-hydroxy-3-O-acyl derivative with an excess of $LiAlH_4$ at room temperature for 30 minutes. The same methods applied to a 1α-hydroxy-3-O-acyl-5,6-trans vitamin D compound provide the 1α-hydroxy-5,6-trans-vitamin D product. Reductive or hydrolytic methods for acyl removal are equally convenient and a choice between them would depend on the nature of other functionalities that may be present in the molecule.

The 5,6-trans-1α-hydroxyvitamin D compounds obtained by this process can, of course, be converted to the 5,6-cis compounds by irradiation with ultraviolet light, according to the general procedures of Inhoffen et al (Chem. Ber. 90, 2544 (1957)). Anaologously the 5,6-trans-1α-hydroxyvitamin D 3-O-acyl intermediates resulting from solvolysis can be converted to the corresponding 5,6-cis-derivatives, which upon acyl removal, as described above, yield the 1α-hydroxyvitamin D compounds.

A noteworthy feature which the present process shares with the original Paaren et al process is its generality. The process may be applied to vitamin D compounds bearing any of the common steroid side chains. More specifically, the side chain R in any of the compounds in Schematic B, may be hydrogen or lower alkyl (such as methyl, ethyl, propyl, isopropyl, butyl, isobutyl), or R may have any of the structures depicted below:

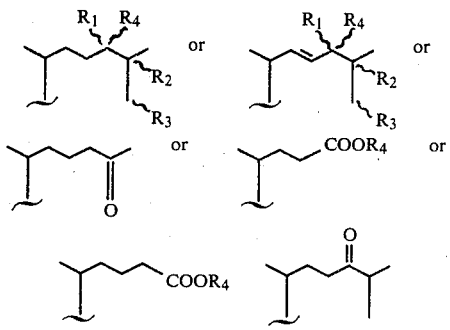

wherein each of $R_1$, $R_2$ and $R_3$ can be hydrogen, hydroxy, lower alkyl O-lower alkyl, O-lower acyl, O-aromatic acyl, or fluoro, and where, $R_4$ is hydrogen or lower alkyl Another noteworthy feature of this invention is that direct solvolysis yield vitamin D compounds and 5,6-trans vitamin D compounds in which the C-3 hydroxy group is specifically aceylated in a more facile manner. Such compounds have considerable utility, particularly in cases where modification (e.g. oxidation, substitution, etc.) at the C-1 hydroxy is desired without affecting the C-3 hydroxy group, the preparation of which by other methods has been generally more cumbersome and difficult.

Wherever in this application and in the claims the term "lower alkyl" is used it is intended to designate a hydrocarbon radical having from 1 to about 5 carbon atoms and which may be of branched or unbranched structure. The term "lower acyl" signifies an acyl group having from 1 to about 4 carbon atoms (e.g. formyl, acetyl, butyryl) and the term "aromatic acyl" means a benzoyl or substituted benzoyl unit (e.g. p-nitro benzoyl).

The following Examples are intended to be illustrative only and are not to be construed as limiting the appended claims.

EXAMPLE 1

A solution of 10 mg of 1α-hydroxy-6-methoxy-3,5-cyclovitamin $D_3$ in 1.0 ml of glacial acetic acid is heated to 55° C. for 15 min. The cooled reaction mixture is added dropwise to a stirring solution of ice/sat $NaHCO_3$ and the resulting neutralized mixture is extracted with ether. The organic extracts are washed once with sat $NaHCO_3$, once with $H_2O$, dried over $MgSO_4$ and the solvent removed in vacuo. The resulting crude oily residue is applied to a 20 cm×20 cm silica gel TLC plate (750μ thick) which is developed in Skellysolve B:ethyl acetate (3:1) to yield 5.8 mg of 1α-hydroxyvitamin $D_3$ 3-acetate [$UV\lambda_{max}$ 264 nm; mass spectrum, m/e: 442 ($M^+$, 40), 382 (65), 364 (15), 269 (20), 134 (100); NMR, δ, 0.54 (3H, s, 18-$H_3$), 0.86 (6H, d, J=6.6 Hz, 26-$H_3$ and 27-$H_3$), 0.92 (3H, d, J=6.0 Hz, 21-$H_3$), 2.04 (3H, s, 3-$OCOCH_3$), 4.41 (1H, m, 1-H), 5.02 (1H, m (sharp), 19(Z)-H), 5.21 (1H, m, 3-H), 5.34 (1H, m (sharp), 19(E)-H), 6.02 (1H, d, J=11.1 Hz, 7-H), 6.34 (1H, d, J=11.1 Hz, 6-H)] and 2.0 mg of 5,6-trans-1α-hydroxyvitamin $D_3$ 3-acetate [$UV\lambda_{max}$ 273 nm; mass spectrum, m/e: 442 ($M^+$, 10), 382 (80), 269 (23), 134 (100); NMR, δ, 0.54 (3H, s, 18-$H_3$), 0.87 (6H, d, J=6.3 Hz, 26-$H_3$ and 27-$H_3$), 0.92 (3H, d, J=6.1 Hz, 21-$H_3$), 2.03 (3H, s, 3-$OCOCH_3$), 4.49 (1H, m, 1-H), 4.99 (1H, m (sharp), 19(Z)-H), 5.13 (1H, m (sharp), 19(E)-H), 5.25 (1H, m, 3-H), 5.80 (1H, d, J=11.4 Hz, 7-H), 6.57 (1H, d, J=11.4 Hz, 6-H)]. Treatment of 1α-hydroxyvitamin $D_3$ 3-acetate with 10% methanolic NaOH in ethanol for 1.0 Hr at 50° C. yields 1α-hydroxyvitamin $D_3$ which is identical to an authentic sample. Similar treatment of 5,6-trans-1α-hydroxyvitamin $D_3$ 3-acetate gives 5,6-trans-1α-hydroxyvitamin $D_3$ [$UV\lambda_{max}$ 273 nm, mass spectrum; m/e: 400 ($M^+$, 12), 382 (8), 152 (42), 134 (100); 0.56 (3H, s, 18-$H_3$), 0.87 (6H, d, J=6.6 Hz, 26-$H_3$ and 27-$H_3$), 0.93 (3H, d, J=6.02 Hz, 21-$H_3$), 4.24 (1H, m, 3-H), 4.50 (1H, m, 1-H), 4.97 (1H, m (sharp), 19(Z)-H), 5.12 (1H, m (sharp), 19(E)-H), 5.89 (1H, d, J=11.4 Hz, 7-H), 6.58 (1H, d, J=11.4 Hz, 6-H).]

EXAMPLE 2

A solution of 8 mg of 1α-dihydroxy-6-methoxy-3,5-cyclovitamin $D_3$ in 800 μl of glacial HOAc is heated to 55° C. for 15 min, cooled, and added dropwise to a stirring mixture of ice/sat $NaHCO_3$. This mixture is extracted with ether and the organic extract is washed once with sat $NaHCO_3$, once with $H_2O$, dried over $MgSO_4$ and concentrated in vacuo. The resultant oil is chromatographed on a 20 cm×20 cm silica gel plate (750μ thickness) which is developed in Skellysolve B:ethyl acetate (3:2) to yield 4.0 mg of 1α,25-dihydroxyvitamin $D_3$ 3-acetate [UV$\lambda_{max}$; mass spectrum, m/e: 458 (M+, 30), 398 (70), 380 (15), 134 (100), 59 (80); NMR, δ, 0.55 (3H, s, 18-$H_3$), 1.22 (6H, s, 26-$H_3$ and 27-$H_3$), 0.92 (3H, d, J=6.0 Hz, 21-$H_3$), 2.04 (3H, s, 3-$OCOCH_3$), 4.38 (1H, m, 1-H), 5.00 (1H, m (sharp), 19(Z)-H), 5.20 (1H, m, 3-H), 5.34 (1H, m (sharp), 19(E)-Z), 6.06 (1H, d, J=11.6 Hz, 7-H), 6.42 (1H, d, J=11.6 Hz, 6-H)] and 1.7 mg of 5,6-trans-1α,25-dihydroxyvitamin $D_3$ 3-acetate [UV$\lambda_{max}$ 273 nm; mass spectrum, m/e: 458 (M+, 10), 398 (85), 380 (25), 134 (100), 59 (85); NMR, δ, 0.54 (3H, s, 18-$H_3$), 1.23 (6H, s, 26-$H_3$ and 27-$H_3$), 0.92 (3H, d, J=6.0 Hz, 21-$H_3$) 2.03 (3H, s, 3-$OCOCH_3$), 4.50 (1H, m, 1-H), 4.96 (1H, m (sharp), 19(Z)-H), 5.10 (1H, m (sharp), 19(E)-H), 5.28 (1H, m, 3-H), 5.80 (1H, d, J=11.4 Hz, 7-H)° 6.55 (1H, 3, J=11.4 Hz, 6-H).] Hydrolysis of 5,6-cis-1α,25-dihydroxyvitamin $D_3$ 3-acetate with 10% NaOH in methanol for 1.0 hr at 55° C. gives 1α,25-dihydroxyvitamin $D_3$ which is identical in all respects to an authentic sample. By treating 5,6-trans-1α,25-dihydroxyvitamin $D_3$ 3-acetate as above, 5,6-trans-1α,25-dihydroxyvitamin $D_3$ is obtained; [UV$\lambda_{max}$ 273 nm; mass spectrum; m/e 416 (15), 398 (8), 152 (40), 134 (100), 59 (95); NMR, δ, 0.55 (3H, s, 18-$H_3$), 1.23 (6H, s, 26-$H_3$ and 27-$H_3$), 0.92 (3H, d, J=6.0 Hz, 21-$H_3$), 4.22 (1H, m, 3-H), 4.53 (1H, m, 1-H), 4.95 (1H, m (sharp), 19(Z)-H), 5.12 (1H, m (sharp), 19(E)-H), 5.85 (1H, d, J=11.4 Hz, 7-H) and 6.55 (1H, d, J=11.4 Hz, 6-H).]

EXAMPLE 3

To a solution of 12 mg of 1α-hydroxy-6-methoxy-3,5-cyclovitamin $D_3$ in 1.0 ml of dry THF is added 1.0 ml of 98% $HCO_2H$. The reaction is heated to 55° C. for 10 min, then quenched with ice/sat. $NaHCO_3$. The aqueous suspension is quickly extracted with ether and the organic extracts are washed with $H_2O$, dried over $MgSO_4$ and concentrated in vacuo. The crude oil is applied to a 20 cm×20 cm silica gel TLC plate (750μ thick) which is developed in Skellysolve B:ethyl acetate (4:1) to yield 6.3 mg of 1α-hydroxyvitamin $D_3$ 3-formate [UV$\lambda_{max}$ 264 nm; mass spectrum, m/e: 428 (M+)] and 2.2 mg of 5,6-trans-1α-hydroxyvitamin $D_3$ 3-formate [UV$\lambda_{max}$ 273; mass spectrum, m/e: 428 (M+)]. Hydrolysis of the formate esters with $KHCO_3$ in aqueous methanol at 45° C. for 0.5 hr gives 1α-hydroxyvitamin $D_3$ and the corresponding 5,6-trans isomer which were identical in all respects to the compounds reported in Example 1.

EXAMPLE 4

A solution of 7.5 mg of 1α,25-dihydroxy-6-methoxy-3,5-cyclovitamin $D_3$ in 1.0 ml of dry THF is treated with 1.0 ml of 98% $HCO_2H$. After heating for 10 min at 55° C. the reaction is quenched over ice sat $NaHCO_3$ and quickly extracted with ether. The ether extracts are washed with water, dried over $MgSO_4$ and concentrated in vacuo. The crude oil is chromatographed on a 20 cm×20 cm silica gel TLC plate (750μ thick) in Skellysolve B:ethyl acetate (3:2) to yield 3.6 mg of 1α,25-dihydroxyvitamin $D_3$ 3-formate [UV$\lambda_{max}$=264 nm; mass spectrum, m/e: 444 (M+)] and 1.3 mg of 5,6-trans-1α,25-dihydroxyvitamin $D_3$ 3-formate: [UV$\lambda_{max}$=273 nm; mass spectrum m/e: 444 (M+)]. Simple $KHCO_3$ hydrolysis of the 5,6-cis and 5,6-trans analog which are identical to the compounds described in Example 2.

EXAMPLE 5

A solution of 380 mg of 1α-hydroxy-6-methoxy-3,5-cyclovitamin $D_2$ in 8 ml of glacial acetic acid is heated to 60° C. for 15 min. The reaction mixture is cooled and slowly added to a stirring solution of ice/sat $NaHCO_3$. After neutralization the aqueous suspension is extracted with ether and the organic phase is washed once with water and then dried over $MgSO_4$. After removing the solvent in vacuo, the crude oily product is applied to a 1.5 cm×60 cm column packed with 45 g of silica gel in hexanes. Batch elution with 100 ml of 4% ethyl acetate, 100 ml of 8% ethyl acetate and 100 ml of 12% ethyl acetate followed by 400 ml of 16% ethyl acetate which was collected in 6.0 ml fractions. Fractions 23–32 contained 180 mg of pure 1α-hydroxyvitamin $D_2$ 3-acetate [UV$\lambda_{max}$=264 nm; mass spectrum, m/e; 454 (M+, 70), 394 (60), 376 (20), 269 (35), 134 (100)] while fractions 33–45 contained a cis-trans mixture and fractions 46–60 contained 60 mg of 5,6-trans-1α-hydroxyvitamin $D_2$ 3-acetate [UV$\lambda_{max}$ 273 nm; mass spectrum, m/e: 454 (M+, 20), 394 (80), 376 (10), 269 (25), 134 (100)]. Hydrolysis of 1α-hydroxy-vitamin $D_2$ 3-acetate with 10% methanolic NaOH in ethanol at 50° C. for 1.0 hr produced 5,6-cis-1α-hydroxyvitamin $D_2$ which is identical in all respects to an authentic sample prepared by another method [Lam et al, Steroids, 30, 671–677 (1977)] and identical hydrolysis of the 5,6-trans isomer gives 5,6-trans-1α-hydroxyvitamin $D_2$ [UV$\lambda_{max}$ 273 nm; mass spectrum, m/e: 412 (25, M+), 394 (60), 376 (10), 269 (20), 152 (60), 134 (100)].

EXAMPLE 6

A solution of 6.8 mg of 1α,25-dihydroxy-6-methoxy-3,5-cyclovitamin $D_2$ (which is prepared from 25-hydroxyvitamin $D_2$, by following the procedures given by Paaren et al (Proc. Nat. Acad. Sci, U.S.A. 75, 2080 (1978)) for the preparation of the corresponding 1α,25-dihydroxy-cyclovitamin $D_3$ analog) in 0.5 ml of glacial acetic acid is heated to 60° for 10 min then added dropwise to an ice/sat $NaHCO_3$ solution. This aqueous mixture is extracted with ether and the organic extracts are washed once with water, dried over $MgSO_4$ and concentrated in vacuo. HPLC of the oily residue on microparticulate silica gel (Zorbax-SIL, a product of DuPont, Wilmington, Del.) with 10% isopropanol in hexane as the solvent yields 3.5 mg of 1α,25-dihydroxyvitamin $D_2$ 3-acetate (UV$\lambda_{max}$ 264 nm; mass spectrum, m/e, 472 (M+) and 412 (M+-60)) and 1.3 mg of 5,6-trans-1α,25-dihydroxyvitamin $D_2$ 3-acetate (UV$\lambda_{max}$ 273 nm; mass spectrum, m/e; 472 (M+), 412 (M+-60)). Hydrolytic cleavage of the 3β-acetoxy functions (5% NaOH/MeOH, 45°, 45 min) provides 1α,25-dihydroxyvitamin $D_2$ which is identical in all respects to an authentic sample and 5,6-trans-1α,25-dihydroxyvitamin $D_2$ (UV,-$\lambda_{max}$ 273 nm; mass spectrum, m/e, 428 (M+).

EXAMPLE 7

A solution of 4.5 mg of 1α,25-trihydroxy-6-methoxy-3,5-cyclovitamin D$_3$ (which is prepared from 24,25-dihydroxyvitamin D$_3$, by tosylation at C-3, solvolysis to the 3,5-cyclovitamin, and SeO$_2$-oxidation to the 1α-hydroxy compound, according to the procedures of Paaren et al, Proc. Nat. Acad. Sci 75, 2080 (1978)) in 0.3 ml of glacial acetic acid is heated to 55° for 10 min and then quenched over ice/sat. NaHCO$_3$. The aqueous solution is extracted with ether and the organic extracts are washed once with water, dried over MgSO$_4$ and concentrated in vacuo. High performance liquid chromatography (HPLC) on micro-particulate silica gel (Zorbax-SIL/DuPont) with 12% isopropanol in hexane as the solvent yields 2.0 mg of 1α,24,25-trihydroxyvitamin D$_3$ 3-acetate (UVλ$_{max}$ 264 nm), and 0.8 mg of the corresponding 5,6-trans-1α,24,25-trihydroxyvitamin D$_3$-acetate isomer (UV,λ$_{max}$ 273 nm). Basic hydrolysis (5% NaOH/MeOH, 45°, 1.0 hr.) of 1α,24,25-trihydroxy-vitamin D$_3$ 3-acetate yields 1α,24,25-trihydroxyvitamin D$_3$ which is identical in all respects to an authentic sample. Hydrolysis of 1α,24,25-trihydroxy-5,6-trans-vitamin D$_3$ under the same conditions give 5,6-trans-1α,24,25-trihydroxyvitamin D$_3$ (UVλ$_{max}$ 273 nm; mass spectrum, m/e, 432 (M+)).

We claim:

1. A method for preparing 1α-hydroxylated vitamin D compounds having the following general formulae

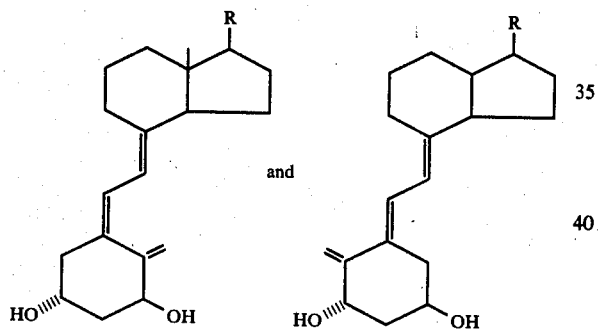

and where R is selected from the group consisting of hydrogen, lower alkyl or from the following groups

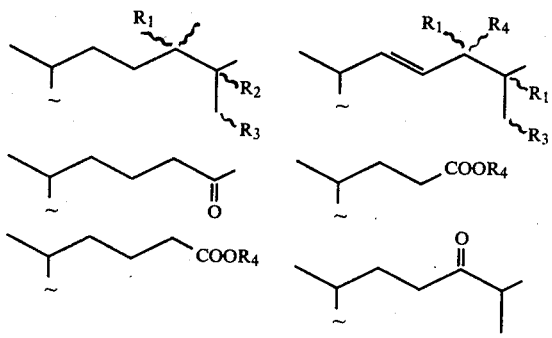

where each of R$_1$, R$_2$ or R$_3$ is selected from the group consisting of hydrogen, hydroxy, lower alkyl, O-lower alkyl, O-lower acyl, O-aromatic acyl or fluoro and where R$_4$ is hydrogen or lower alkyl which comprises subjecting a 1α-hydroxy-cyclovitamin D compounds having the general formula

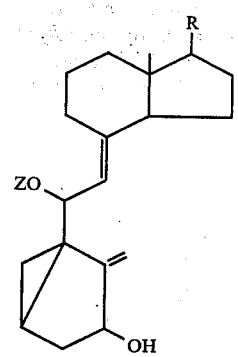

where Z is hydrogen or lower alkyl
where R is selected from the group consisting of hydrogen, lower alkyl or from the following groups

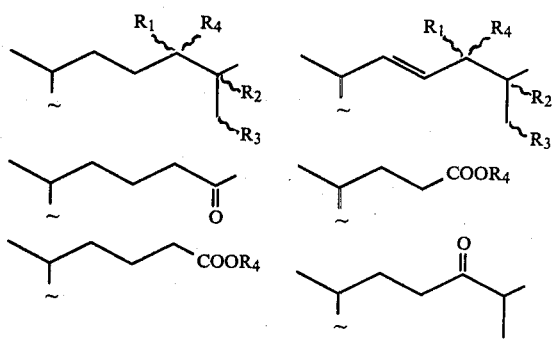

where each of R$_1$, R$_2$ or R$_3$ is selected from the group consisting of hydrogen, hydroxy, lower alkyl, O-lower alkyl, O-lower acyl, O-aromatic acyl or fluoro and where R$_4$ is hydrogen or lower alkyl to solvolysis in the presence of a low molecular weight organic carboxylic acid having up to about two carbon atoms recovering a mixture containing the 1α-hydroxy-3-O-acyl vitamin D and the corresponding 5,6-trans-1α-hydroxy-3-O-acyl-vitamin D compounds and removing the 3-O-acyl group from said compounds by subjecting them to base-catalyzed hydrolysis or hydride reduction.

2. The method of claim 1 wherein the 1α-hydroxy-3-O-acyl vitamin D compound is separated from the solvolysis mixture prior to removal of the 3-O-acyl group.

3. The method of claim 1 wherein the 5,6-trans-1α-hydroxy-3-O-acyl vitamin D compound is separated from the solvolysis mixture prior to removal of the 3-O-acyl group.

4. The process of claim 1 wherein the low molecular weight organic carboxylic acid is formic acid.

5. The process of claim 1 wherein the low molecular weight organic carboxylic acid is acetic acid.

6. The process of claim 1 in which the cyclovitamin D compound subjected to solvolysis is 1α-hydroxy-6-methoxy-3,5-cyclovitamin D$_3$.

7. The process of claim 1 in which the cyclovitamin D compound subjected to solvolysis is 1α-hydroxy-6-methoxy-3,5-cyclovitamin D$_2$.

8. The process of claim 1 in which the cyclovitamin D compound subjected to solvolysis is 1α,25-dihydroxy-6-methoxy-3,5-cyclovitamin $D_3$.

9. The process of claim 1 in which the cyclovitamin D compound subjected to solvolysis is 1α,25-dihydroxy-6-methoxy-3,5-cyclovitamin $D_2$.

10. The process of claim 1 in which the cyclovitamin D compound subjected to solvolysis is 1α,24,25-trihydroxy-6-methoxy-3,5-cyclovitamin $D_3$.

11. 5,6-trans-1α-hydroxyvitamin $D_2$.

12. 5,6-trans-1α,25-hydroxyvitamin $D_2$.

* * * * *

UNITED STATES PATENT OFFICE
CERTIFICATE OF CORRECTION

Patent No. 4,260,549          Dated April 7, 1981

Inventor(s) Hector F. DeLuca et al

It is certified that error appears in the above-identified patent and that said Letters Patent are hereby corrected as shown below:

In Column 13, Claim 1, the depiction of the side chain groups designated by R, should be

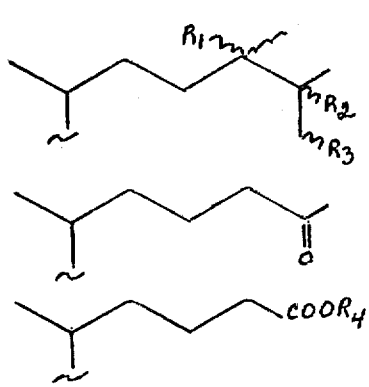

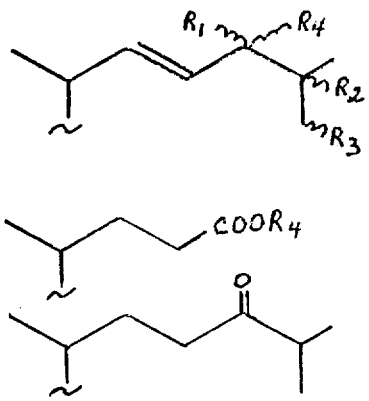

Signed and Sealed this

Thirtieth Day of June 1981

[SEAL]

*Attest:*

*Attesting Officer*

RENE D. TEGTMEYER

*Acting Commissioner of Patents and Trademarks*